(12) United States Patent
Fujita et al.

(10) Patent No.: US 7,790,450 B2
(45) Date of Patent: Sep. 7, 2010

(54) EXPRESSION VECTOR, A TRANSFORMANT CARRYING THE SAME AND A METHOD FOR PRODUCING HETEROLOGOUS PROTEIN

(75) Inventors: Yasuko Fujita, Chiyoda-ku (JP); Hideki Tohda, Chiyoda-ku (JP); Yuko Hama, Chiyoda-ku (JP)

(73) Assignee: Asahi Glass Company, Limited, Tokyo (JP)

( * ) Notice: Subject to any disclaimer, the term of this patent is extended or adjusted under 35 U.S.C. 154(b) by 164 days.

(21) Appl. No.: 12/037,117

(22) Filed: Feb. 26, 2008

(65) Prior Publication Data

US 2008/0286833 A1 Nov. 20, 2008

Related U.S. Application Data

(63) Continuation of application No. PCT/JP2006/316752, filed on Aug. 25, 2006.

(30) Foreign Application Priority Data

Aug. 29, 2005 (JP) .............................. 2005-247819

(51) Int. Cl.
C12N 15/63 (2006.01)
C12N 15/85 (2006.01)
C12P 21/00 (2006.01)

(52) U.S. Cl. .................... 435/320.1; 435/325; 435/71.1

(58) Field of Classification Search .................. None
See application file for complete search history.

(56) References Cited

FOREIGN PATENT DOCUMENTS

| EP | 1 223 219 A2 | 7/2002 |
|---|---|---|
| JP | 07-163373 | 6/1995 |
| JP | 2776085 | 5/1998 |
| JP | 10-234375 | 9/1998 |
| JP | 11-192094 | 7/1999 |
| JP | 2000-136199 | 5/2000 |
| JP | 2000-262284 | 9/2000 |
| JP | 2002-503709 | 2/2002 |
| WO | 96/23890 | 8/1996 |

OTHER PUBLICATIONS

Taricani et al (Nucleic Acid Research, 2001, vol. 29, No. 14, pp. 3030-3040).*
Edited by Hajime Ishikawa et al., Saibo Seibutsugaku Jiten, Kabushiki Kaisha Asakura Shoten, Feb. 25, 2005 (pp. 349, 380 to 383).
Kayser KJ, et al., Inducible and constitutive expression using new plasmid and integrative expression vectos for Thermus sp., Lett. Appl. Microbiol., 2001, vol. 32, No. 6, p. 412-418.
Chen D, et al., Global transcriptional responses of fission yeast to environmental stress., Mol. Biol. Cell, 2003, vol. 14, No. 1, p. 214-229.
Yuko Giga-Hama and Kumagai, eds., Foreign gene expression in fission yeast *Schizosaccharomyces pombe*, Springer-Verlag, (1997).
Ricardo G. Maggi, et al., "Regulated Expression of Green Fluorescent Protein in *Debaryomyces hansenii*", Journal of Industrial Microbiology & Biotechnology, vol. 31 , No. 7, XP002553073, Aug. 2004, pp. 301-310.
Yasuko Fujita, et al., "Heat Shock-Inducible Expression Vectors for Use in *Schizosaccharomyces pombe*", Fems Yeast Research, vol. 6, No. 6, XP002553074, May 4, 2006, pp. 883-887.
Attila Adam, et al., "Heat-Inducible Expression of a Reporter Gene Detected by Transient Assay in Zebrafish", Experimental Cell Research, vol. 256, No. 1, XP 002553075, Apr. 10, 2000, pp. 282-290.
Jean-Paul Cadoret, et al., "Promoters from Drosophila Heat Shock Protein and Cytomegalovirus Drive Transient Expression of Luciferase Introduced by Particle Bombardment into Embryos of the Oyster *Crassostrea gigas*", Journal of Biotechnology, vol. 56, No. 3, XP002553076, Aug. 28, 1997, pp. 183-189.

* cited by examiner

*Primary Examiner*—Celine X Qian
(74) *Attorney, Agent, or Firm*—Oblon, Spivak, McClelland, Maier & Neustadt, L.L.P.

(57) ABSTRACT

To provide a heterologous protein expression system which enables the fission yeast *Schizosaccharomyces pombe* as a host to produce of a heterologous protein which is almost impossible to express, or if possible, produced at low levels, under control of conventional promoters.

The present invention provides an expression for use in the fission yeast *Schizosaccharomyces pombe*, a transformant carrying the expression vector, a method for producing a heterologous protein using the transformant, in particular a method for producing a heterologous protein in which a heat shock protein gene promoter in *Schizosaccharomyces pombe* is used to regulate gene expression by application of a specific form of stress, whereby the timing of the production of the desired heterologous protein can be controlled.

7 Claims, 2 Drawing Sheets

SEQUENCE LISTING

<160> NUMBER OF SEQ ID NOS: 6

<210> SEQ ID NO 1
<211> LENGTH: 29
<212> TYPE: DNA
<213> ORGANISM: Artificial Sequence -continued

```
<220> FEATURE:
<223> OTHER INFORMATION: Primer

<400> SEQUENCE: 1
gtttaagctt catatggtga gcaagggcg                                29

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
gttttctcga gttacttgta cagctcgtcc                               30

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
gtttggatcc aacaagctgt aaaatagcgg                               30

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
gtttggatcc aagagcgata gcttccgtcg                               30

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
gtttggatcc gtgcatgagc aacaattgcg                               30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
gtttcatatg ttaaaattta aacaattgcg                               30
```

EXPRESSION VECTOR, A TRANSFORMANT CARRYING THE SAME AND A METHOD FOR PRODUCING HETEROLOGOUS PROTEIN

TECHNICAL FIELD

The present invention relates to an expression vector for use in the fission yeast *Schizosaccharomyces pombe*, a transformant of *Schizosaccharomyces pombe* carrying the expression vector, and a method for producing a heterologous protein using the transformant, in particular to a method for producing a heterologous protein in which a heat shock protein gene promoter in *Schizosaccharomyces pombe* is used to regulate gene expression by application of a specific form of stress, whereby the timing of the production of the desired heterologous protein can be controlled.

BACKGROUND ART

The yeast *Schizosaccharomyces pombe* (hereinafter referred to as *S. pombe*) is phylogenetically quite different from the budding yeast. It is greatly different from other yeasts in the chromosomal structure and the mechanisms of genome replication, RNA splicing, transcription, post-translational modification and the like and is rather analogous to animal cells in some of these mechanisms. Therefore, it is widely used as a model eukaryote (Non-patent Document 1).

Because of its various characteristics, *S. pombe* is considered as a unicellular eukaryote closer to higher animal cells and is a very useful yeast as a host for expression of foreign genes, especially genes from higher animals. In particular, it is known to be suitable for expression of genes from animals such as human (Patent Documents 1 to 7).

For expression of a heterologous protein in *S. pombe* hosts, it is required that a promoter directs transcription of foreign genes encoding the heterologous protein. As the promoter, endogenous promoters for *S. pombe* genes and promoters from other organisms or viruses have been used. As promoters presently used for expression of heterologous proteins in *S. pombe* hosts, gene promoters such as the endogenous adl promoter in *S. pombe* (for constitutive expression), the fbp1 promoter, the inv1 promoter (repressible by glucose: Patent Document 5), the ctr4 promoter (repressible by copper ions) and the nmt1 promoter (repressible by thiamine) and virus promoters such as the hCMV, SV40, CaMV promoters (for constructive expression) are known.

Patent Document 1: JP-B-2776085
Patent Document 2: JP-A-07-163373
Patent Document 3: WO96/23890
Patent Document 4: JP-A-10-234375
Patent Document 5: JP-A-11-192094
Patent Document 6: JP-A-2000-136199
Patent Document 7: JP-A-200-262284
Non-patent Document 1: Giga-Hama and Kumagai, eds., Foreign gene expression in fission yeast *Schizosaccharomyces pombe*, Springer-Verlag, (1997)

DISCLOSURE OF THE INVENTION

Problems that the Invention is to Solve

As mentioned above, only several promoters including *S. pombe* and viral promoters are available for expression of heterologous proteins by way of genetic engineering. In addition, they have drawbacks such as inability to regulate expression (the adh1, hCMV, SV40 and CaMV promoters), a long induction time (the nmt1 promoter), the need of change in the medium composition during cell cultivation for induction (the nmt1, fbp1, inv1 and ctr4 promoters) and the need of coexpression of a repressor for complete repression (the CaMV modified promoter).

Means for Solving the Problems

Considering the above, the present inventors conducted research in search of a promoter which allows better control of gene expression and, as a result, found that use of the promoter for the heat shock protein gene in *S. pombe* allows efficient production of heterologous proteins. The present invention has been accomplished on the basis of this discovery. Namely, the present invention provides:

1. An expression vector for production of a heterologous protein in *Schizosaccharomyces pombe* as a host, which comprises a promoter of a heat shock protein gene in *Schizosaccharomyces pombe* and a foreign gene to be governed by the promoter.
2. The expression vector according to 1, wherein the heat shock protein gene is hsp16.
3. The expression vector according to 2, wherein the promoter of hsp16 consists of a region of at least 100 bp long upstream of the 5' end of the ORF of hsp16.
4. A method of constructing an expression vector for production of a heterologous protein in *Schizosaccharomyces pombe* as a host, which is characterized by introducing a promoter of a heat shock protein in *Schizosaccharomyces pombe* and a foreign gene to be governed by the promoter into a multicloning vector for *Schizosaccharomyces pombe*.
5. A transformant obtained by transforming *Schizosaccharomyces pombe* with the expression vector as defined in 1, 2 or 3.
6. A transformant obtained by transforming *Schizosaccharomyces pombe* with a vector constructed by the method as defined in 4.
7. A method of producing a heterologous protein, which comprises growing the transformant as defined in 5 or 6 and harvesting the produced heterologous protein.
8. The method of producing a heterologous protein according to 7, wherein after the transformant is cultured, an inductive stimulus is given to the transformant to induce production of the heterologous protein.
9. The method of producing a heterologous protein according to 8, wherein the inductive stimulus is heat stress.
10. The method of producing a heterologous protein according to 8 or 9, wherein the inductive stimulus is addition of at least one member selected from cadmium, an osmotic pressure increasing agent, hydrogen peroxide and ethanol.

Effect of the Invention

Most of the currently used gene expression systems for *S. pombe* hosts require replacement of the growth medium or depletion of repressors (such as glucose) in the medium in order to induce expression. In contrast, the heat shock protein promoter in the present invention can be induced rapidly when heat stress is given to the cells by exposing them to a temperature higher than their growth temperature. Further, the promoter can be induced by other forms of stress such as an osmotic pressure increasing agent, hydrogen peroxide, ethanol and the like and has the advantage that the induction method can be selected according to the properties of the host (for example, heat sensitivity). Therefore, the gene expression system of the present invention using the promoter is both simple and versatile and therefore a very useful gene expression system.

BEST MODE FOR CARRYING OUT THE INVENTION

Figure 1:
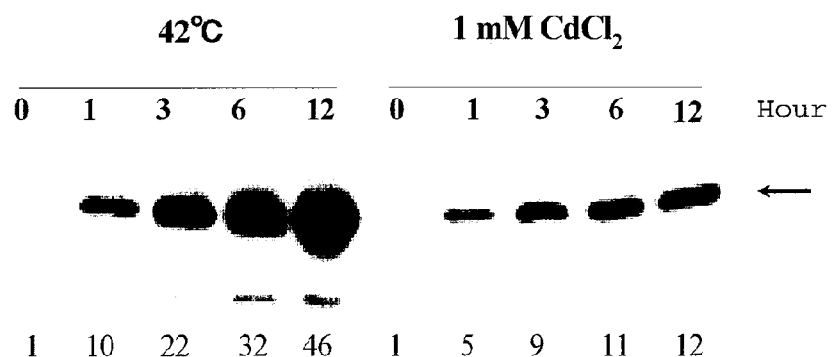
FIG. 1 Induction of GFP expression under heat stress or cadmium stress. The arrow on the right indicates the molecular weight of GFP, about 27 kDa, and the figures underneath indicate approximate relative signal intensities in relation to the signal intensity at 0 hour.

The heterologous protein produced using the expression vector system of the present invention is a protein extrinsic to the host, and in the present invention using a *S. pombe* host, it is a protein extrinsic to *S. pombe*. The heterologous protein in the present invention is preferably a protein produced by multicellular organisms such as animals and plants, especially a protein produced by a mammal (inclusive of human), though there are no particular restrictions. Such a protein is rarely obtained with high activity by a prokaryotic host microorganism such as *E. coli* and, if obtained by using an animal cell line such as CHO as the host, is produced very inefficiently. The expression system for use *S. pombe* hosts is considered to solve these problems.

Heat shock protein (hsp) is a generic name for proteins which are induced to be synthesized when the cell or the individual is suddenly exposed to a temperature 5-10° C. higher than its physiological temperature (heat shock) and function as a chaperon to protect proteins from thermal denaturation or aggregation. In vivo synthesis of heat shock proteins is induced by various chemical substances such as electron transport chain inhibitors, transition metals, SH reagents and ethanol as well as by heat shock. In the present invention, the system of the present invention allows choice from these possible factors of inductive stimuli to induce protein synthesis. A particularly preferred inductive stimulus is heat stress, for example, heat shock. Addition of cadmium, an osmotic pressure increasing agent, hydrogen peroxide or ethanol can also give a preferable inductive stimulus.

Heat shock proteins are widely conserved from bacteria to higher animals. A database containing the sequences of *S. pombe* genes is known (*S. pombe* GeneDB; http://www.genedb.org/genedb/pombe/), and the fission yeast has at least 17 genes classified as heat shock protein genes. Among these 17 genes, hsp16 (SPBC3E7.02c) encoding a low-molecular-weight heat shock protein is induced most strongly in a wild-type *S. pombe* strain under heat stress at 39° C. Microarray analyses revealed that application of heat stress increases its expression level by a factor of about 70 (D. Chen et al. Mol. Biol. Cell 14 (2003), 214-229).

The promoter of a heat shock protein gene in the present invention is the promoter of one of these heat shock protein genes, preferably the promoter of the above-mentioned hsp16 (hereinafter referred to as the hsp16 promoter). Further, when the hsp16 promoter is used as the promoter of a heat shock protein gene, it is preferred to use a region of at least 1000 bp long upstream of the 5' end of the hsp16 ORF. The hsp16 regulatory region is 1800 bp long from the 5' end of the hsp16 ORF. Therefore, as the hsp16 promoter, a region of 1000-1800 bp long upstream of the 5' end of the ORF is preferably used.

As specific protocols for construction of the expression vector of the present invention, known specific protocols, for example, those disclosed in a reference publication [J. Sambrook et al., "Molecular Cloning 2nd ed.", Cold Spring Harbor Laboratory Press (1989)], may be used. The foreign gene encoding the above-mentioned heterologous protein is always inserted into the vector so as to be under the control of the promoter of a heat shock protein gene. In the present invention, it is preferred to use a multicloning vector for *S. pombe* as the vector.

Multicloning vectors are vectors having a multicloning site, and introduction of a desired foreign gene at the multicloning site gives an expression vector. Expression vectors are vectors carrying a foreign gene and used for expression of the heterologous protein encoded by the foreign gene. In expression vectors, the promoter gene is placed upstream of the gene of the heterologous protein and regulates the expression of the gene. In the case of multicloning vectors, because the gene of the heterologous protein is introduced at the multicloning site, the inducible promoter gene is placed upstream of the multicloning site.

In the present invention, because the promoter gene is an endogenous promoter gene in *S. pombe*, *S. pombe* is best suited as the host to be transformed with the expression vector. The *S. pombe* strain to be used in the present invention may, for example, be ATCC38399 (leu1-32h-) or ATCC38436 (ura4-294h-), which is available from the American Type Culture Collection. *S. pombe* can be transformed by using an expression vector by known methods, for example, the lithium acetate method [K. Okazaki et al., Nucleic Acids Res., 18, 6485-6489 (1990)].

A transformant obtained by transforming *S. pombe* with the expression vector of the present invention grows with no (or little) expression of the heterologous protein under normal growth conditions (with no stress such as heat stress). At this stage with no burden of expressing the heterologous protein, it can grow more efficiently to a large cell number than when it is under the burden of expressing the heterologous protein.

When the transformant is grown with an inductive stimulus such as heat stress, the promoter is activated to direct transcription of the heterologous protein under its control, and the heterologous protein is expressed. Under growth conditions with an inductive stimulus, it usually grows slower than under normal conditions, but because it has already grown to a large cell number in the previous stage, the culture system as a whole produces a large amount of the heterologous protein. Heat stress is one of available inductive stimuli, and other inductive stimuli may be used as long as their effects are verified as mentioned above. An inductive stimulus is preferably heat, or addition of cadmium, an osmotic pressure increasing agent, hydrogen peroxide, ethanol or the like.

In the case of heat, heat stress is applied by a temperature increase of at least 5° C., preferably 10° C. from the original culture temperature. To give heat stress, the temperature can be increased to the maximum survival temperature of *S. pombe*. Therefore, to give heat stress, the culture temperature is raised by at least 5° C., preferably at least 10° C., to a temperature of 30-55° C., preferably 35-50° C., particularly preferably 40-45° C., from the original culture temperature. It takes at least several minutes before the effect of heat stress is confirmed, and heat stress is applied for 1-29 hours, preferably 1-15 hours though there are no particular restrictions.

In the case of addition of cadmium, it is added in the form of cadmium ions. A preferable, though non-restrictive, example is cadmium chloride. The final cadmium concentration is from 0.1 to 1.5 mM, preferably from 0.5 to 1.0 mM. The incubation time is preferably at most 5 hours, particularly preferably at most 3 hours.

In the case of an osmotic pressure increasing agent, an osmotic pressure increasing agent such as a high concentration electrolyte or sorbitol is added to increase the osmotic pressure. A preferable, though non-restrictive, example is high concentration potassium chloride. The final potassium concentration is from 0.1 to 2.0 M, preferably from 0.5 to 1.5 M. The treatment time is preferably from 1 to 12 hours, particularly preferably from 1 to 10 hours, though there are no particular restrictions.

In the case of hydrogen peroxide, its final concentration is from 0.1 to 1.5 mM, preferably from 0.5 to 1.9 mM. The incubation time is preferably from 1 to 15 hours, particularly preferably from 1 to 12 hours, though there are no particular restrictions.

In the case of ethanol, its final concentration is from 5 to 20 V/V %, preferably from 5 to 15 V/V %. The incubation time is preferably from 1 to 20 hours, particularly preferably from 1 to 15 hours, though there are no particular restrictions.

The above-mentioned conditions may be applied alone or in combination. The combined effect can easily be confirmed by comparing the expression levels.

Thus, it is possible to produce heterologous proteins more efficiently by growing S. pombe while controlling heterologous protein expression by inductive stimuli such as stress conditions. The control enables more efficient production of a heterologous protein which is almost impossible to express, or if possible, produced at low levels, under control of conventional promoters.

The transformant is grown in a known medium, and nutrient media such as YPD medium [M. D. Rose et al., "Methods In Yeast Genetics", Cold Spring Harbor Laboratory Press (1990)], minimal media such as MB Medium [K. Okazaki et al., Nucleic Acids Res., 18, 6485-6489 (1990)] and the like may be used. The transformant is grown usually at from 16 to 42° C., preferably at from 25 to 37° C., for from 8 to 168 hours, preferably from 48 to 96 hours. Either of shaking culture and stationary culture can be employed, and if necessary, the culture medium may be stirred or aerated.

The cultured transformant cells are ruptured sonically or mechanically to obtain a cell extract containing the desired heterologous protein, from which the desired heterologous protein is isolated and purified. If the desired heterologous protein is secreted from the cells, the desired heterologous protein is can be isolated and purified from the culture medium (see WO96/23890).

As isolation and purification methods for obtaining the protein product, known methods, such as methods utilizing difference in solubility such as salting out and solvent precipitation, methods utilizing difference in molecular weight such as ultrafiltration and gel electrophoresis, methods utilizing difference in electric charge such as ion-exchange chromatography, methods utilizing specific affinity such as affinity chromatography, methods utilizing difference in hydrophobicity such as reverse phase high performance liquid chromatography, and methods utilizing difference in isoelctric point such as isoelectric focusing may be mentioned.

The isolated and purified protein can be identified by conventional methods such as western blotting or assay of its activity. The structure of the purified protein can be defined by amino acid analysis, amino-terminal analysis, primary structure analysis and the like.

EXAMPLES

Now, the present invention will be described in further detail with reference to Examples. However, it should be understood that these Examples merely illustrate the best mode, and the present invention is by no means restricted thereto.

<Construction of Gene Expression System>

A vector for heterologous protein expression was constructed using the hsp promoter, an endogenous heat shock protein gene promoter in S. pombe, and GFP (green fluorescent protein) as the heterologous protein. A GFP DNA fragment was amplified by PCR using pEGFP-N1 (CLONTECH) as the template, an upstream primer carrying HindIII and NdeI sites at the 5' end and a downstream primer carrying an XhoI site at the 5' end. The primer sequences are shown in Table 1 (GFPS and GFPAS) (SEQ ID NOS: 1 and 2).

The amplified DNA fragment was digested with HindIII and XhoI and inserted at the multicloning site of a subcloning vector, pBS-SK+ (STRATAGENE), and the plasmid was digested with BamHI and NdeI. A DNA fragment of about 1800 bp long was amplified by PCR using a region upstream of the hsp16 translation initiation site in the fission yeast strain ARC039 (see Morita et al., which will be mentioned later) as the template, an upstream primer carrying a BamHI site at the 5' end and a downstream primer carrying NdeI site at the 5' end (Table 1, −1.8S and hsp16AS) (SEQ ID NOS: 3 and 6). The amplified DNA fragment was digested with BamHI and NdeI, and introduced into the pBS-SK+ carrying the GFP gene. The hsp16 promoter+GFP fragment was then excised from pBS-SK+ by digestion with XhoI and NotI and inserted at the multicloning site of an expression vector for fission yeast, pAL-(SK+) (Morita et al., which will be mentioned later). The ARC039 strain was transformed with the plasmid by the simple transformation method developed by Morita et al. (T. Morita and K. Takegawa. Yeast 21 (2004), 613-617) to obtain a transformant.

TABLE 1

Primer Sequences
(the lowercase letters are restriction sites)

| | | |
|---|---|---|
| GFPS | 5'-gtttaagcttcatATGGTGAGCAA GGGG-3' | (SEQ ID NO: 1) |
| GFPAS | 5'-gttttctcgagTTACTTGTACAGC TCGTCC-3' | (SEQ ID NO: 2) |
| −1.8S | 5'-gtttggatccAACAAGCTGTAAAA TAGCGG-3' | (SEQ ID NO: 3) |
| −1.2S | 5'-gtttggatccAAGAGCGATAGCTT CCGTCG-3' | (SEQ ID NO: 4) |
| −0.6S | 5'-gtttggatccGTGCATGAGCAACA ATTGCG-3' | (SEQ ID NO: 5) |
| hsp16AS | 5'-gtttcatatgTTAAAATTTAAACA ATTGCG-3' | (SEQ ID NO: 6) |

<Induction of Heterologous Protein Expression by Heat or Cadmium Stress>

The transformant obtained above was examined for induction of GFP expression by heat stress. Further, because hsp16 expression is also strongly induced by cadmium (D. Chen et al. Mol. Biol. Cell 14 (2003), 214-229.), the transformant was also examined for induction of GFP expression by cadmium stress. The transformant was grown at 28° C. to the early logarithmic phase (OD600=about 0.3) in a selective liquid medium (MM-Leu; EMM medium containing uracil, arginine, lysine, glutamic acid, histidine and adenine at a final concentration of 75 μg/ml). The transformant was shifted to a temperature of 42° C., and then incubation was continued with shaking. Alternatively, cadmium chloride was added at a final concentration of 1 mM, and then the incubation was continued at 28° C. with shaking. After 0, 1, 3, 6 and 12 hours of stress application, aliquots of cells were harvested, beaten with glass beads and subjected to total protein extraction. The GFP amounts in the respective samples were determined by Western analysis following SDS-PAGE on 12% acrylamide gel with a total protein load of 20 μg for each lane and compared.

Under heat stress, the GFP expression started to increase within 1 hour and continued to increase until it reached about 46 times the initial expression level at 12 hours, as shown in FIG. 1. Under cadmium stress, though the GFP expression almost plateaued within 3 hours, it increased by about 12 times during 12 hours of cadmium stress application.

<Induction of Heterologous Protein Expression by Various Forms of Stress Other than Heat and Cadmium>

Induction of GFP expression by various stimuli other than heat and cadmium was investigated. The transformant was grown at 28° C. to the early logarithmic phase (OD600=about 0.3) in a selective medium (MM-Leu) and was dispensed in 5 ml aliquots. 1 mM Mercury chloride, 1 mM manganese chloride, 1 mM ferric chloride, 1 mM silver nitrate, 1 mM zinc chloride, 0.8 M sodium chloride, 0.5 M lithium chloride, 1 M potassium chloride, 10 mM calcium chloride, 0.5 mM hydrogen peroxide, 10 mM caffeine, 10% ethanol and 1 M sorbitol were added to the respective aliquots in terms of final concentration, and the incubation of the transformant was continued at 28° C. with shaking. The cells were harvested 3 hours after application of the respective inductive stimuli and observed under a microscope.

Figure 2:
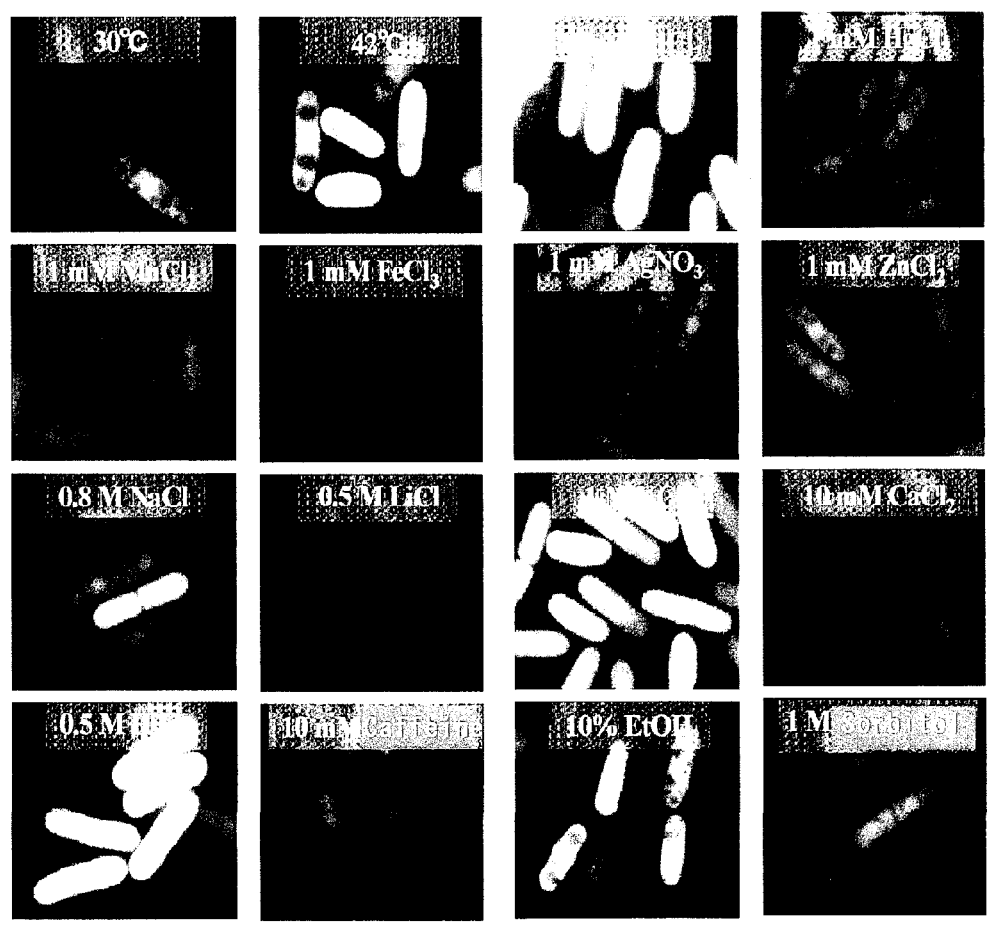
FIG. 2 Induction of GFP expression under various forms of stress.

GFP production was strongly induced by potassium chloride, hydrogen peroxide and ethanol, as induced by heat and cadmium, as shown in FIG. 2.

<Induction of Heterologous Protein Expression by Potassium Chloride, Hydrogen Peroxide and Ethanol>

GFP expression induction under various forms of stress such as potassium chloride, hydrogen peroxide and ethanol was investigated by Western analysis. 1 M Potassium chloride, 0.5 mM hydrogen peroxide and 10 V/V % ethanol were added to three cultures grown to the early logarithmic phase (OD600=about 0.3) in a selective liquid medium (MM-Leu) at 28° C., respectively, and incubation was continued with shaking. After 0, 1, 3 6 and 12 hours of stress application, aliquots of cells were harvested, and the GFP amounts in the respective samples were determined by Western analysis and compared, as previously mentioned.

Figure 3:
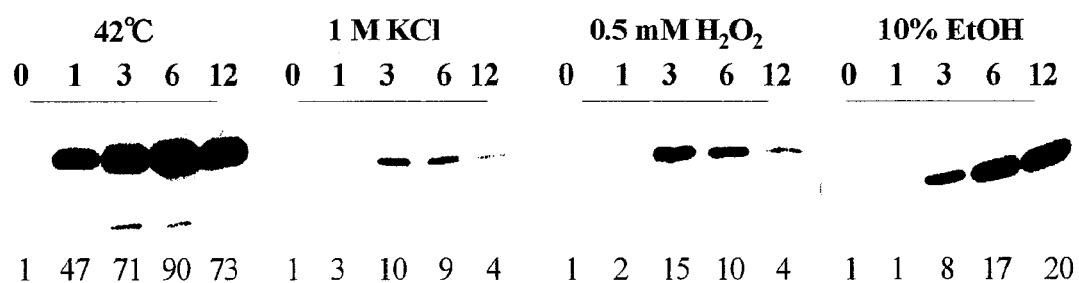
FIG. 3 Induction of GFP expression by heat, potassium chloride, hydrogen peroxide and ethanol. The figures underneath indicate approximate relative signal intensities in relation to the signal intensity at 0 hour.

GFP expression was strongly induced by potassium chloride, hydrogen peroxide and ethanol, though less than by heat stress, and increased from 10 to 20 times, as shown in FIG. 3.

<Length of the hsp16 Promoter Region Required for Regulation of Gene Expression>

The length of the hsp16 promoter region required for regulation of expression of a downstream gene was investigated. DNA fragments of about 1200 bp and about 600 bp long were amplified by PCR using a region upstream of the translation initiation site in genomic DNA from the ARC039 strain as the template, upstream primers carrying a BamHI site at the 5' end (Table 1, −1.2 S and −0.6 S) (SEQ ID NOS: 4 and 5) and the previously mentioned downstream primer hsp16AS.

Gene fragments carrying the 1200 bp or 600 bp promoter region followed the GFP gene were constructed as described previously and introduced at the multicloning site of an expression vector for fission yeast pAL-(SK+), and the vectors were transformed into the ARC039 strain. The resulting transformants were grown at 28° C. to the early logarithmic phase (OD600=about 0.3) in a selective liquid medium (MM-Leu) and shifted to a temperature of 42° C., and incubation was continued with shaking. After 0, 1, (3), 6 and 12 hours of stress application, aliquots of cells were harvested, and the GFP amounts in the samples were determined by Western analysis and compared.

Figure 4:
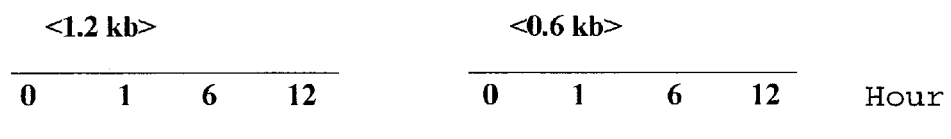
FIG. 4 Induction of GFP expression under heat stress under control of hsp16 promoter regions of various lengths.

As shown in FIG. 4, under control of the 1200 bp region, GFP expression was suppressed at ordinary temperature and induced strongly by heat stress, like it was under control of the 1800 bp region. In contrast, under control of the 600 bp region, GFP expression was observed at high levels when cells were grown at ordinary temperature, and no increase in expression level was observed under heat stress. The results indicate that in order for the hsp 16 promoter to regulate a downstream gene, the 600 bp region upstream of the translation initiation site is insufficient, and the 1200 bp region allows regulation of gene expression. Therefore, it seems preferred to use a region of at least 1000 bp long upstream of the 5' end of the hsp16 ORF.

INDUSTRIAL APPLICABILITY

As described above, the promoter of the present invention can be induced readily when heat stress is given to the cells. Further, because it is induced by not only heat stress but also other forms of stress, it has the advantage that the induction method can be selected according to the properties of the host. Therefore, the gene expression vector of the present invention using the promoter is both simple and versatile and therefore a very useful gene expression system.

The entire disclosure of Japanese Patent Application No. 2005-247819 filed on Aug. 29, 2005 including specification, claims, drawings and summary is incorporated herein by reference in its entirety.

What is claimed is:

1. An expression vector for production of a heterologous protein in *Schizosaccharomyces pombe*, which comprises a hsp16 promoter isolated from *Schizosaccharomyces pombe*, wherein the promoter consists of 1000 base pairs nucleic acid sequence immediately upstream of the 5' end of the open reading frame of the hsp16 gene; and a foreign gene operably linked to the promoter.

2. A method of constructing an expression vector for production of a heterologous protein in *Schizosaccharomyces pombe* as a host, the method comprising introducing a hsp16 promoter of a heat shock protein in *Schizosaccharomyces pombe*, wherein the promoter consists of a region of 1000 base pairs upstream of the 5' end of the open reading frame of the heat shock protein gene; and a foreign gene governed by the promoter into a multicloning vector suitable for expression in *Schizosaccharomyces pombe*.

3. A transformant obtained by transforming *Schizosaccharomyces pombe* with the expression vector as defined in claim 1.

4. A method of producing a heterologous protein, which comprises growing the transformant as defined in claim 3 and harvesting the produced heterologous protein.

5. The method of producing a heterologous protein according to claim 4, wherein after the transformant is grown, an inductive stimulus is given to the transformant to induce production of the heterologous protein.

6. The method of producing a heterologous protein according to claim 5, wherein the inductive stimulus is heat stress.

7. The method of producing a heterologous protein according to claim 5, wherein the inductive stimulus is addition of at least one member selected from the group consisting of cadmium, an osmotic pressure increasing agent, hydrogen peroxide and ethanol.

* * * * *